United States Patent
Brettin et al.

(10) Patent No.: US 9,129,039 B2
(45) Date of Patent: Sep. 8, 2015

(54) SCENARIO DRIVEN DATA MODELLING: A METHOD FOR INTEGRATING DIVERSE SOURCES OF DATA AND DATA STREAMS

(71) Applicant: UT-Battelle, LLC, Oak Ridge, TN (US)

(72) Inventors: Thomas S. Brettin, Knoxville, TN (US); Robert W. Cottingham, Oak Ridge, TN (US); Shelton D. Griffith, Jackson, MS (US); Daniel J. Quest, Knoxville, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 2 days.

(21) Appl. No.: 13/654,152

(22) Filed: Oct. 17, 2012

(65) Prior Publication Data

US 2013/0124574 A1    May 16, 2013

Related U.S. Application Data

(60) Provisional application No. 61/548,319, filed on Oct. 18, 2011.

(51) Int. Cl.
*G06F 17/30* (2006.01)
*G06F 19/28* (2011.01)
*G06F 19/00* (2011.01)

(52) U.S. Cl.
CPC .......... *G06F 17/30958* (2013.01); *G06F 19/28* (2013.01); *G06F 19/3493* (2013.01)

(58) Field of Classification Search
CPC .................................................. G06F 19/3493
See application file for complete search history.

(56) References Cited

U.S. PATENT DOCUMENTS

| | | | | |
|---|---|---|---|---|
| 6,761,312 B2 * | 7/2004 | Piatek et al. | ................... | 235/385 |
| 6,766,277 B2 * | 7/2004 | Siegel | ............................. | 702/187 |
| 6,803,202 B2 * | 10/2004 | Sullivan et al. | ............... | 435/7.92 |
| 6,838,993 B2 * | 1/2005 | Beiswenger et al. | ....... | 340/573.5 |
| 7,024,370 B2 * | 4/2006 | Epler et al. | ......................... | 705/3 |

(Continued)

FOREIGN PATENT DOCUMENTS

WO    WO2008/013553    *    1/2008    ................ G06F 7/00

OTHER PUBLICATIONS

Belleau F, Nolin M, Tourigny N, Rigault P, Morissette J. Bio2RDF: Towards a mashup to build bioinformatics knowledge systems. Journal of Biomedical Informatics. 2008;41(5):706-716. doi: 10.1016/j.jbi.2008.03.004.*

(Continued)

*Primary Examiner* — Mariela Reyes
*Assistant Examiner* — Edward Jacobs
(74) *Attorney, Agent, or Firm* — Scully, Scott, Murphy & Presser, P.C.

(57) ABSTRACT

A system and method of integrating diverse sources of data and data streams is presented. The method can include selecting a scenario based on a topic, creating a multi-relational directed graph based on the scenario, identifying and converting resources in accordance with the scenario and updating the multi-directed graph based on the resources, identifying data feeds in accordance with the scenario and updating the multi-directed graph based on the data feeds, identifying analytical routines in accordance with the scenario and updating the multi-directed graph using the analytical routines and identifying data outputs in accordance with the scenario and defining queries to produce the data outputs from the multi-directed graph.

16 Claims, 6 Drawing Sheets

(56) References Cited

U.S. PATENT DOCUMENTS

| | | | |
|---|---|---|---|
| 7,249,006 B2* | 7/2007 | Lombardo et al. | 703/2 |
| 7,399,276 B1* | 7/2008 | Brown et al. | 600/300 |
| 7,457,731 B2* | 11/2008 | Rao | 703/2 |
| 7,705,723 B2* | 4/2010 | Kahn et al. | 340/521 |
| 7,792,779 B2* | 9/2010 | Dash | 706/52 |
| 7,817,046 B2* | 10/2010 | Coveley et al. | 340/573.1 |
| 7,840,421 B2* | 11/2010 | Gerntholtz | 705/3 |
| 8,335,298 B2* | 12/2012 | Clawson | 379/45 |
| 8,519,850 B2* | 8/2013 | Reinpoldt | 340/573.1 |
| 8,560,339 B2* | 10/2013 | Khan | 705/2 |
| 2002/0120408 A1* | 8/2002 | Kreiswirth et al. | 702/20 |
| 2002/0193967 A1* | 12/2002 | Siegel | 702/187 |
| 2003/0009239 A1* | 1/2003 | Lombardo et al. | 700/30 |
| 2003/0114986 A1* | 6/2003 | Padmanabhan et al. | 702/1 |
| 2003/0129578 A1* | 7/2003 | Mault | 435/4 |
| 2003/0194350 A1* | 10/2003 | Stamatelos et al. | 422/83 |
| 2003/0204130 A1* | 10/2003 | Colston et al. | 600/300 |
| 2004/0015372 A1* | 1/2004 | Bergman et al. | 705/3 |
| 2004/0024612 A1* | 2/2004 | Gerntholtz | 705/2 |
| 2004/0073459 A1* | 4/2004 | Barthell | 705/2 |
| 2004/0116821 A1* | 6/2004 | Beiswenger et al. | 600/549 |
| 2005/0055188 A1* | 3/2005 | Prior et al. | 703/11 |
| 2005/0055330 A1* | 3/2005 | Britton et al. | 707/1 |
| 2005/0060189 A1* | 3/2005 | Zhang | 705/2 |
| 2005/0203681 A1* | 9/2005 | Minor, Jr. | 701/23 |
| 2006/0036619 A1* | 2/2006 | Fuerst et al. | 707/100 |
| 2006/0161392 A1* | 7/2006 | Sholl et al. | 702/183 |
| 2007/0090942 A1* | 4/2007 | Berry | 340/521 |
| 2007/0222599 A1* | 9/2007 | Coveley et al. | 340/572.4 |
| 2008/0107652 A1* | 5/2008 | Durvasula et al. | 424/135.1 |
| 2008/0109761 A1* | 5/2008 | Stambaugh | 715/853 |
| 2008/0139890 A1* | 6/2008 | Craine et al. | 600/300 |
| 2008/0155440 A1* | 6/2008 | Trevor et al. | 715/769 |
| 2008/0177571 A1* | 7/2008 | Rooney et al. | 705/2 |
| 2008/0221965 A1* | 9/2008 | Riddle | 705/9 |
| 2008/0301120 A1* | 12/2008 | Zhu et al. | 707/5 |
| 2009/0035736 A1* | 2/2009 | Wolpert et al. | 434/219 |
| 2009/0070898 A1* | 3/2009 | Allen et al. | 800/286 |
| 2009/0172511 A1* | 7/2009 | Decherd et al. | 715/207 |
| 2009/0276753 A1* | 11/2009 | Bouillet et al. | 717/105 |
| 2010/0145902 A1* | 6/2010 | Boyan et al. | 706/54 |
| 2011/0046920 A1* | 2/2011 | Amis | 702/181 |
| 2011/0130636 A1* | 6/2011 | Daniel et al. | 600/301 |
| 2011/0158946 A1* | 6/2011 | Durvasula et al. | 424/93.2 |
| 2012/0154139 A1* | 6/2012 | Dupoteau | 340/539.1 |
| 2013/0226948 A1* | 8/2013 | Ahn et al. | 707/758 |

OTHER PUBLICATIONS

McEntyre J, Ostell J, editors. The NCBI Handbook [Internet]. Bethesda (MD): National Center for Biotechnology Information (US); 2002-. Available from: http://www.ncbi.nlm.nih.gov/books/NBK21101/, accessed Nov. 19, 2013, PDF with excerpts imported into OACS.*

Kitts, Paul. "Genome Assembly and Annotation Process." The NCBI Handbook, U.S. National Library of Medicine, Aug. 13, 2003, Web, Apr. 23, 2014, http://www.ncbi.nlm.nih.gov/books/NBK21086/.*

Ostell, Jim. "The Entrez Search and Retrieval System" The NCBI Handbook, U.S. National Library of Medicine, Aug. 13, 2003, Web, Apr. 23, 2014, https://www.ncbi.nlm.nih.gov/books/NBK21081/.*

Tatusova, T.A., Madden, T.L. (1999) BLAST2 sequences, a new tool for comparing protein and nucleotide sequences. FEMS Microbiol. Lett. 174, 247-250.*

* cited by examiner

```
                        SEQUENCE LISTING

<160> NUMBER OF SEQ ID NOS: 3

<210> SEQ ID NO 1
<211> LENGTH: 104
<212> TYPE: PRT
<213> ORGANISM: Artificial Sequence
<220> FEATURE:
<223> OTHER INFORMATION: Synthetic Peptide

<400> SEQUENCE: 1

Met Gly Gly Met Asp Ala Leu His Ala Ala Gly Ile Ala Thr Tyr Ala
1               5                   10                  15

Asn Ala Leu Ser Asn Gln Leu Ala Pro Gln Glu Gly Met Val Ala Ala
                20                  25                  30

Gln His Ser Leu Thr Phe Ala Ala Asn Gly Trp Val Glu Pro Ala Thr
            35                  40                  45

Ala Pro Asn Phe Gly Pro Leu Lys Val Phe Tyr Pro Gly Pro Gly His
        50                  55                  60

Thr Ser Asp Asn Ile Thr Val Gly Ile Asp Cys Ser Asp Ile Ala Phe
65                  70                  75                  80

Gly Gly Cys Leu Ile Lys Asp Ser Lys Ala Lys Ser Leu Gly Asn Leu
                85                  90                  95

Gly Asp Ala Asp Thr Glu His Tyr
            100

<210> SEQ ID NO 2
<211> LENGTH: 270
<212> TYPE: PRT
<213> ORGANISM: Artificial Sequence
<220> FEATURE:
<223> OTHER INFORMATION: Synthetic Peptide

<400> SEQUENCE: 2

Met Glu Leu Pro Asn Ile Met His Pro Val Ala Lys Leu Ser Thr Ala
1               5                   10                  15

Leu Ala Ala Ala Leu Met Leu Ser Gly Cys Met Pro Gly Glu Ile Arg
                20                  25                  30

Pro Thr Ile Gly Gln Gln Met Glu Thr Gly Asp Gln Arg Phe Gly Asp
            35                  40                  45

Leu Val Phe Arg Gln Leu Ala Pro Asn Val Trp Gln His Thr Ser Tyr
        50                  55                  60

Leu Asp Met Pro Gly Phe Gly Ala Val Ala Ser Asn Gly Leu Ile Val
65                  70                  75                  80

Arg Asp Gly Gly Arg Val Leu Val Val Asp Thr Ala Trp Thr Asp Asp
                85                  90                  95
```

-continued

```
Gln Thr Ala Gln Ile Leu Asn Trp Ile Lys Gln Glu Ile Asn Leu Pro
            100                 105                 110

Val Ala Leu Ala Val Val Thr His Ala His Gln Asp Lys Met Gly Gly
            115                 120                 125

Met Asp Ala Leu His Ala Ala Gly Ile Ala Thr Tyr Ala Asn Ala Leu
130                 135                 140

Ser Asn Gln Leu Ala Pro Gln Glu Gly Met Val Ala Ala Gln His Ser
145                 150                 155                 160

Leu Thr Phe Ala Ala Asn Gly Trp Val Glu Pro Ala Thr Ala Pro Asn
                165                 170                 175

Phe Gly Pro Leu Lys Val Phe Tyr Pro Gly Pro Gly His Thr Ser Asp
            180                 185                 190

Asn Ile Thr Val Gly Ile Asp Gly Thr Asp Ile Ala Phe Gly Gly Cys
            195                 200                 205

Leu Ile Lys Asp Ser Lys Ala Lys Ser Leu Gly Asn Leu Gly Asp Ala
            210                 215                 220

Asp Thr Glu His Tyr Ala Ala Ser Ala Arg Ala Phe Gly Ala Ala Phe
225                 230                 235                 240

Pro Lys Ala Ser Met Ile Val Met Ser His Ser Ala Pro Asp Ser Arg
                245                 250                 255

Ala Ala Ile Thr His Thr Ala Arg Met Ala Asp Lys Leu Arg
                260                 265                 270

<210> SEQ ID NO 3
<211> LENGTH: 158
<212> TYPE: PRT
<213> ORGANISM: Artificial Sequence
<220> FEATURE:
<223> OTHER INFORMATION: Synthetic Peptide

<400> SEQUENCE: 3

Leu Asp Met Pro Gly Phe Gly Ala Val Ala Ser Asn Gly Leu Ile Val
1               5                   10                  15

Arg Asp Gly Gly Arg Val Leu Val Val Asp Thr Ala Trp Thr Asp Asp
            20                  25                  30

Gln Thr Ala Gln Ile Leu Asn Trp Ile Lys Gln Glu Ile Asn Leu Pro
            35                  40                  45

Val Ala Leu Ala Val Val Thr His Ala His Gln Asp Lys Met Gly Gly
            50                  55                  60

Met Asp Ala Leu His Ala Ala Gly Ile Ala Thr Tyr Ala Asn Ala Leu
65                  70                  75                  80

Ser Asn Gln Leu Ala Pro Gln Glu Gly Met Val Ala Ala Gln His Ser
                85                  90                  95

Leu Thr Phe Ala Ala Asn Gly Trp Val Glu Pro Ala Thr Ala Pro Asn
            100                 105                 110

Phe Gly Pro Leu Lys Val Phe Tyr Pro Gly Pro Gly His Thr Ser Asp
            115                 120                 125

Asn Ile Thr Val Gly Ile Asp Gly Thr Asp Ile Ala Phe Gly Gly Cys
            130                 135                 140

Leu Ile Lys Asp Ser Lys Ala Lys Ser Leu Gly Asn Leu Gly
145                 150                 155
```

SCENARIO DRIVEN DATA MODELLING: A METHOD FOR INTEGRATING DIVERSE SOURCES OF DATA AND DATA STREAMS

CROSS REFERENCE TO RELATED APPLICATION

The present invention claims the benefit of U.S. provisional patent application 61/548,319 filed Oct. 18, 2011, the entire contents and disclosure of which are incorporated herein by reference.

STATEMENT REGARDING FEDERALLY SPONSORED RESEARCH OR DEVELOPMENT

This invention was made with government support under Prime Contract No. DE-AC05-00OR22725 awarded by the U.S. Department of Energy. The government has certain rights in the invention.

BACKGROUND

Online blogs, social media, journals, and hyper-link technology all provide means for inputting information as text. However, manual effort is required to relate information. Examples in bio-surveillance include ProMed mail. OBO foundry is an example of ontology research in the biological sciences (http://www.obofoundry.org/, and "A core ontology on events for representing occurrences in the real world"). Medical EcoSystem—Personalized Event-Based Surveillance Deliverable D4.1 (M-Eco) has a report that outlines aspects of the state of the art in bio-surveillance. Further, such kind of data is not usually streamed, instead it is used in analysis. There also exists the concept of a 'mashup' or "purpose driven, customized data integrations that facilitate question answering on a topic of interest" as described in "Building an HIV data mashup using Bio2RDF".

BRIEF SUMMARY OF THE DISCLOSURE

The present disclosure, in one aspect, illustrates strategies for integrating DNA sequence data in near real time. A need for a system and method of the present disclosure may deal with complicated, heterogeneous data and may integrate multi-relational directed graphs with data streams, and may advance the concept of mashups.

A novel system and method for integrating diverse sources of data and data streams is presented. The method in one aspect may include selecting a scenario based on a topic, creating a multi-relational directed graph based on the scenario, identifying and converting resources in accordance with the scenario and updating the multi-directed graph based on the resources, identifying data feeds in accordance with the scenario and updating the multi-directed graph based on the data feeds, identifying analytical routines in accordance with the scenario and updating the multi-directed graph using the analytical routines and identifying data outputs in accordance with the scenario and defining queries to produce the data outputs from the multi-directed graph.

The system for integrating diverse sources of data and data streams, in one aspect, may include a processor, such as a CPU or another integrated circuit, or the like, and a module operable to select a scenario based on a topic, create a multi-relational directed graph based on the scenario, identify and convert resources in accordance with the scenario and update the multi-directed graph based on the converted resources, identify data feeds in accordance with the scenario and update the multi-directed graph based on the data feeds, identify analytical routines in accordance with the scenario and update the multi-directed graph using the analytical routines, and identify data outputs in accordance with the scenario and define queries to produce the data outputs from the multi-directed graph.

In one aspect, selecting a scenario may include creating detectors operable to continuously provide data related to the topic, and obtaining one or more of particular text in accordance with the scenario, geo-location information associated with the particular text and a number of times of occurrence of the particular text. In one aspect, identifying and converting resources may include converting the resources into HTML and linking the converted resources into the multi-relational directed graph. In one aspect, identifying analytical routines may include using the sensors to compare sequences in a data stream based on alignment, performing analysis between entities of the multi-relational directed graph, literals and ontologies, and linking the entities to samples.

A machine-readable data storage device storing a program of instructions executable by a machine to perform one or more methods described herein also may be provided.

BRIEF DESCRIPTION OF THE DRAWINGS

The invention is further described in the detailed description that follows, by reference to the noted drawings by way of non-limiting illustrative embodiments of the invention, in which like reference numerals represent similar parts throughout the drawings. As should be understood, however, the invention is not limited to the precise arrangements and instrumentalities shown. In the drawings.

DETAILED DESCRIPTION

Biology is rapidly becoming a data intensive, data-driven science. Data should be represented and connected in ways that best represent its full conceptual content and allow both automated integration and data driven decision-making. Recent advancements in distributed multi-relational directed graphs, implemented in the form of the Semantic Web, make it possible to deal with complicated heterogeneous data in new and interesting ways.

The present disclosure presents scenario driven data modelling (SDDM), which is a new approach for dealing with complicated, heterogeneous data that integrates multi-relational directed graphs with data streams. SDDM may further advance the concept of mashups. In SDDM, a Semantic Model may be created. Data feeds may be matched to the model in near real time, and when the model matches the data in the stream, an alert may be generated that allows humans to query the model and a stored version of the data that matches the model.

Figure 1:
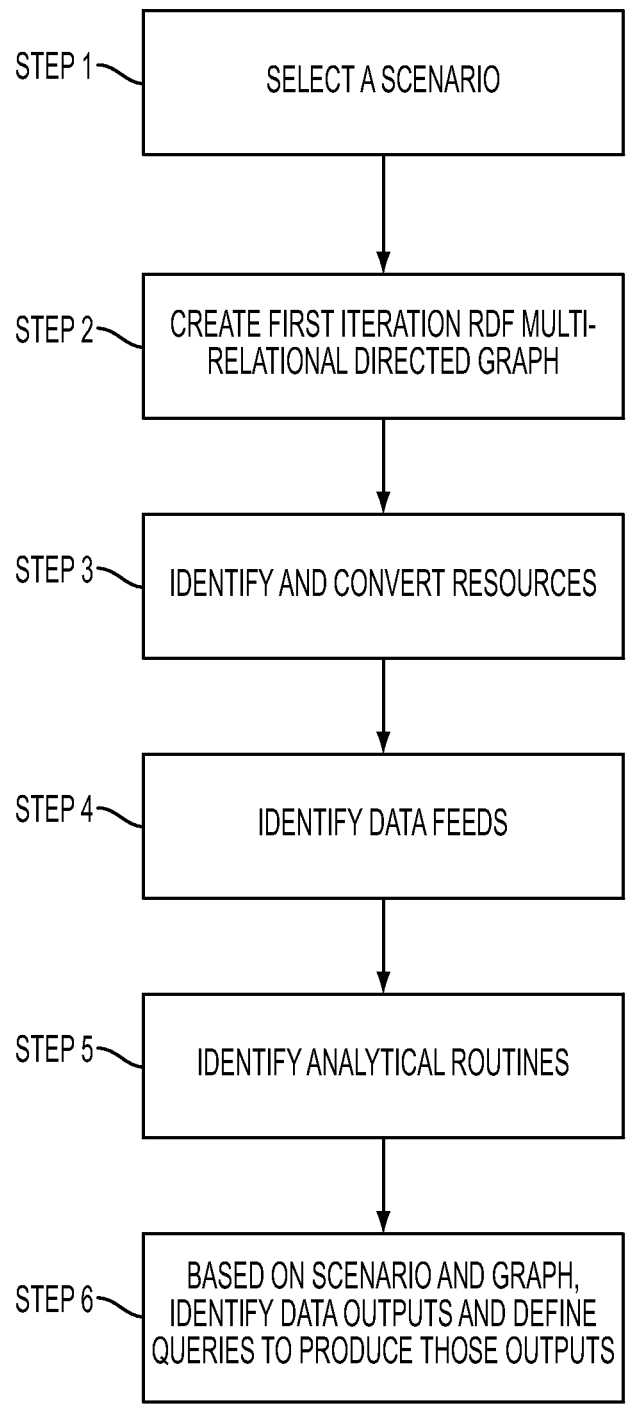
FIG. 1 is a flow diagram illustrating a method of integrating diverse sources of data and data streams in one embodiment of the present invention.

FIG. 1 shows a flow diagram, e.g., high level steps of SDDM in one embodiment which may include the following:
Step 1: Select a scenario for refinement based on a topic to be examined or explored;
Step 2: Create first iteration of a resource description framework (RDF) multi-relational directed graph;
Step 3: Identify those resources required by the scenario but absent in the Semantic Web and convert the resources to the RDF;
Step 4: Identify data feeds;
Step 5: Identify analytical routines for comparing information in the data stream to the concepts outlined in the scenario;
Step 6: Based on the scenario and the resulting multi-relational directed graph (MRDG), identify the data outputs that meet the decision support needs of the end user and define queries to produce those outputs.

SDDM can be applied to virtually any data integration challenge with widely divergent types of data and data streams. One embodiment provides an example of a process in which SDDM is applied to a complex data integration challenge. The SDDM process created a model of the emerging New Delhi metallo-beta-lactamase gene (NDM-1) health threat, identified and filled gaps in that model, and constructed reliable software that monitored data streams based on the scenario derived multi-relational directed graph. Integrating genetics data with reports from traditional media can be explored. In particular, the SDDM process constructed a scenario, created a RDF multi-relational directed graph that linked diverse types of data to the Semantic Web, implemented RDF conversion tools (RDFizers) to bring content into the Semantic Web, identified data streams and analytical routines to analyse those streams, and identified user requirements and graph traversals to meet end-user requirements.

The SDDM process significantly reduced the software requirements phase by letting the scenario and resulting multi-relational directed graph define what is possible and then set the scope of the user requirements. Approaches like SDDM enhance the future of data intensive, data-driven science because they automate the process of converting massive data streams into usable knowledge.

Next generation DNA sequencers and online social media produce a data deluge requiring new tools for storage, representation, visualization, querying, interaction, and integration Data streams are leading to interesting observations. Google™ used a single information source, the search logs of terms entered by users, to predict a recent flu outbreak nearly two weeks ahead of the CDC. Developing more powerful methods requires integration of multiple information sources and connecting it in ways that are timely, relevant, and capable of distinguishing useful information from noise. Some of these capabilities have been explored in simulation systems that model the spread of disease. There is a pressing need for a bio-security system that will do this in near real time.

BioSITES

The Biological Signature Identification and Threat Evaluation System (BioSITES) is an effort to develop a secure, authoritative, predictive and complete reference standard for bio-threat detection and mitigation that will support detection research and development and lead to near real-time bio-surveillance and bio-threat identification. BioSITES is being developed at Oak Ridge National Laboratory; the work discussed herein is part of the BioSITES effort.

BioSITES implements methodologies that deal with complex bio-surveillance data integration requirements. No single institution owns all of the data necessary for bio-surveillance. It is highly heterogeneous and requires petabytes of storage space. The BioSITES knowledgebase is being constructed assuming that the data infrastructure will be composed of multiple distributed and interoperable data repositories serving as reference catalogs. The work, in one aspect, focuses on the principles for constructing a semantic knowledgebase capable of integrating diverse data repositories and data streams. The section below titled 'The BioSITES Streaming Data Kernel' provides an overview of how data streams through the BioSITES system and clarifies requirements of the BioSITES knowledgebase.

The Data Integration Challenge

Bio-surveillance requires rapid integration of vastly different types of information. Resources such as the Antibiotic Resistance Genes Database, MvirDB, SuperToxic, and PIG—the pathogen interaction gateway are all excellent examples of molecular catalogues used in bio-surveillance applications. These repositories can be combined with geo-location, time and important information from the literature to form a model of the entities and relationships involved as a disease spreads. A key challenge is to codify this heterogeneous data and information in a computationally useful manner that meets bio-surveillance requirements. Typically, the first step is to integrate the data in a semantically consistent data model.

In bioinformatics, dominant approaches to heterogeneous data integration include: (1) an operational data store such as Chado, where heterogeneous data is integrated into a unified model by importing each data source into a unified relational schema, and (2) 'knuckles-and-nodes', where data is distributed and integrated through the use of ontologies. BioSITES requires the ability to integrate heterogeneous data streams, and distributed reference catalogs, making an ontology centric approach more appropriate.

The knuckles-and-nodes approach is also used in the Semantic Web. The Semantic Web is to data what the World Wide Web is to documents, a globally linked data store where data elements are distributed across multiple servers on the Internet. The Semantic Web's representation is a multi-relational directed graph (MRDG) implemented through the resource description framework (RDF). A large part of the Semantic Web, relevant to genetics and biology has been constructed by the Bio2RDF project and this vast resource was used in the construction of BioSITES.

The present disclosure introduces scenario driven data modelling (SDDM). SDDM is a data integration process that defines the required relationships between diverse sources of data, data streams, and software components. SDDM is related to the concept of data mashups or "purpose driven, customized data integrations that facilitate question answering on a topic of interest". Scenarios (defined further in the section 'Scenarios') are like mashups, they are purpose driven and use similar integration strategies, but are larger in scope and complexity because they include analytical methods and software components designed for analysing data that exists outside the Semantic Web. These analytical methods and software components analyse data as a stream, and when they find matches, they integrate data into the Semantic Web.

People consume content on the web. To navigate the web, a person starts with one article, and then navigates to other articles, building an interpretation of the world as he or she follows hyperlinks, consumes additional content, and perhaps 'teleports' randomly to other articles and topics. Data is presented on the web when it is typically embedded into human readable hypertext marked up language (HTML) or images and served on request. As the amount of data available is exploding, it is increasingly likely that people traversing the web will miss important content. Machines need to be used to help augment human search capabilities and reduce the time it takes to find and communicate important information. However, with data represented in free text, machine interpretation may be limited because no general-purpose way has been discovered to compile natural language down to a level understood by computer programs. It is however possible to write simpler software with very limited goals that has a limited understanding of free text; search engines are good examples of such software.

In the present disclosure in one embodiment, the Semantic Web is used as a platform for bio-defense. Internationally, professionals and researchers are currently developing assays, assembling information, coordinating prevention efforts, notifying first responders and the media, and identifying and characterizing new pathogens. While each of these efforts has merit, specialization tends to create silos where individuals who need to communicate with each other may not connect because they have not identified the value in the connection. A top down solution to this problem is to build cross-cutting communities focused on integrative approaches. A bottom up approach to the problem uses social networks to connect individuals and focus on specific problems. Both of these approaches are important, but focus on solving integration problems through people and personal connections. In both approaches, software systems are isolated systems, integration of information takes place in the humans who use these systems. Near real time bio-threat prevention and detection may require integrated software systems.

A more powerful alternative approach to isolated systems may be an integrated and global platform that includes the Semantic Web and its capabilities to ascribe meaning to and draw inferences from data. SDDM allows automated integration methods that become extremely useful when dealing with large, complex streaming data that otherwise would not be humanly possible to accurately and reliably integrate. SDDM enables distillation of massive data amounts and computing of analyses into a set of facts and a resolution of their accuracy for decision making. The RDF data representation also accommodates changes in representation and ownership beyond what has been previously possible.

Utilizing SDDM, a system is defined and constructed that integrates heterogeneous data based on a bio-surveillance scenario that operates in near real-time, meeting scenario requirements. The SDDM process, along with the example of its implementation presented herein, represents an iterative refinement of a data integration process. SDDM combines data feeds, private and public data stored in files or databases and the Semantic Web. SDDM starts with a scenario, or free text description, and then gradually updates the scenario into a multi-relational-directed graph encoded in RDF. Data stored in flat files or databases is integrated by constructing software called RDFizers (defined in more detail below and in the glossary) that convert traditional data representations into multi-relational-directed graphs (a collection of RDF statements). RDFizers have been built for ProMed to link molecular concepts to time and geo-location. Resources available on the Semantic Web (e.g. Bio2RDF) can be used to link molecular concepts to DNA and protein sequences.

The SDDM process also integrates streaming data. The resulting exemplary software enables streaming data from genetic sequencers to be compared to sequences identified in Bio2RDF, and, when a match is found, RDF statements integrate the new findings into the Semantic Web. This data integration approach was applied to the construction of a near real-time and completely automated analysis system capable of monitoring the NDM-1 gene globally. This proof of concept further illustrates the power and flexibility of ontology-centric data integration approaches.

The BioSITES Streaming Data Kernel

Figure 2:
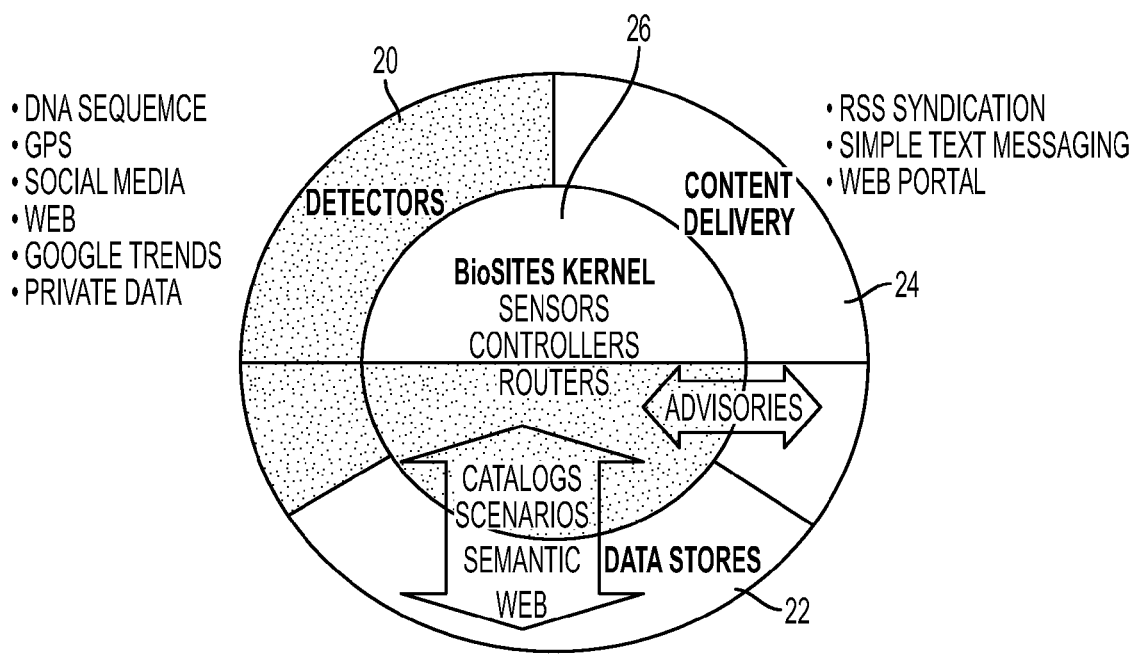
FIG. 2 illustrates a modular view of the BioSITES Architecture in one embodiment of the present invention.

The BioSITES streaming kernel looks at feeds of data and attempts to match elements in the knowledgebase to data in the stream. If data in the stream is matched to specific elements in the catalog, then an advisory is published to alert first responders and analysts. These advisories feed the decision support system. The system architecture may comprise four subsystems: data feed generation (detectors), data stores (catalogs), content delivery (advisories) and the streaming kernel. FIG. 2 illustrates a module view of the BioSITES architecture that shows the system's principal components in one embodiment. As shown in FIG. 2, subsystems, e.g., Detectors 20, Data Stores 22, Content Delivery 24, and the BioSITES Kernel 26, are utilized to realize systems for monitoring streaming data. The BioSITES Kernel 26 is at the heart of the architecture, providing monitoring capabilities. Each of the other subsystems 20, 22, 24 may include a functioning kernel to run. Subsystems interact with the BioSITES kernel through clearly defined interfaces.

BioSITES detectors feed a massive amount of data continuously to the BioSITES system. Example feeds include web crawlers, DNA sequencing machines, logistics information, weather sensors, and satellite imagery. As this information streams past the BioSITES system, useful connections and knowledge are automatically extracted and then integrated directly into the Semantic Web or presented to users.

There are many combinations of data important in situational awareness and response, and the methodologies and systems disclosed in the present disclosure may be applicable to those many combinations of data. As an example, the methodology and system of the present disclosure in one embodiment are explained below with reference to data integration dealing with time (date the events took place), space (geo-location of where the event occurred) and genetics (the molecular components of the outbreak/attack).

Scenarios

A BioSITES scenario is a structured description of a malicious action or series of actions that causes harm or disruption in health, the economy, or day-to-day activities in people, crops and/or livestock. A scenario could be based on real world events or be hypothetical. A scenario need not be confined to a specific organism or spread mechanism, but these could be attributes of a specific scenario. Outside of the bio-security arena, a scenario could be used to improve public health by addressing naturally occurring pathogens.

A scenario identifies the downstream data users and uses, which drive data collection and refinement requirements. BioSITES scenarios are concerned with identifying data streams that provide temporal, spatial and sequence information when combined. A scenario is used to scope the software development process. For example, a scenario may require one or more catalogs that are later used by sensors of the BioSITES Kernel 26. A scenario also identifies possible data streams that will be monitored and algorithms that can be used in monitoring those data streams. A scenario may be extremely specific or more general in the way that it references data stream elements and catalogs. For example, a scenario could state 'a toxin was used' instead of 'Botulinum toxin was used'.

Figure 3:
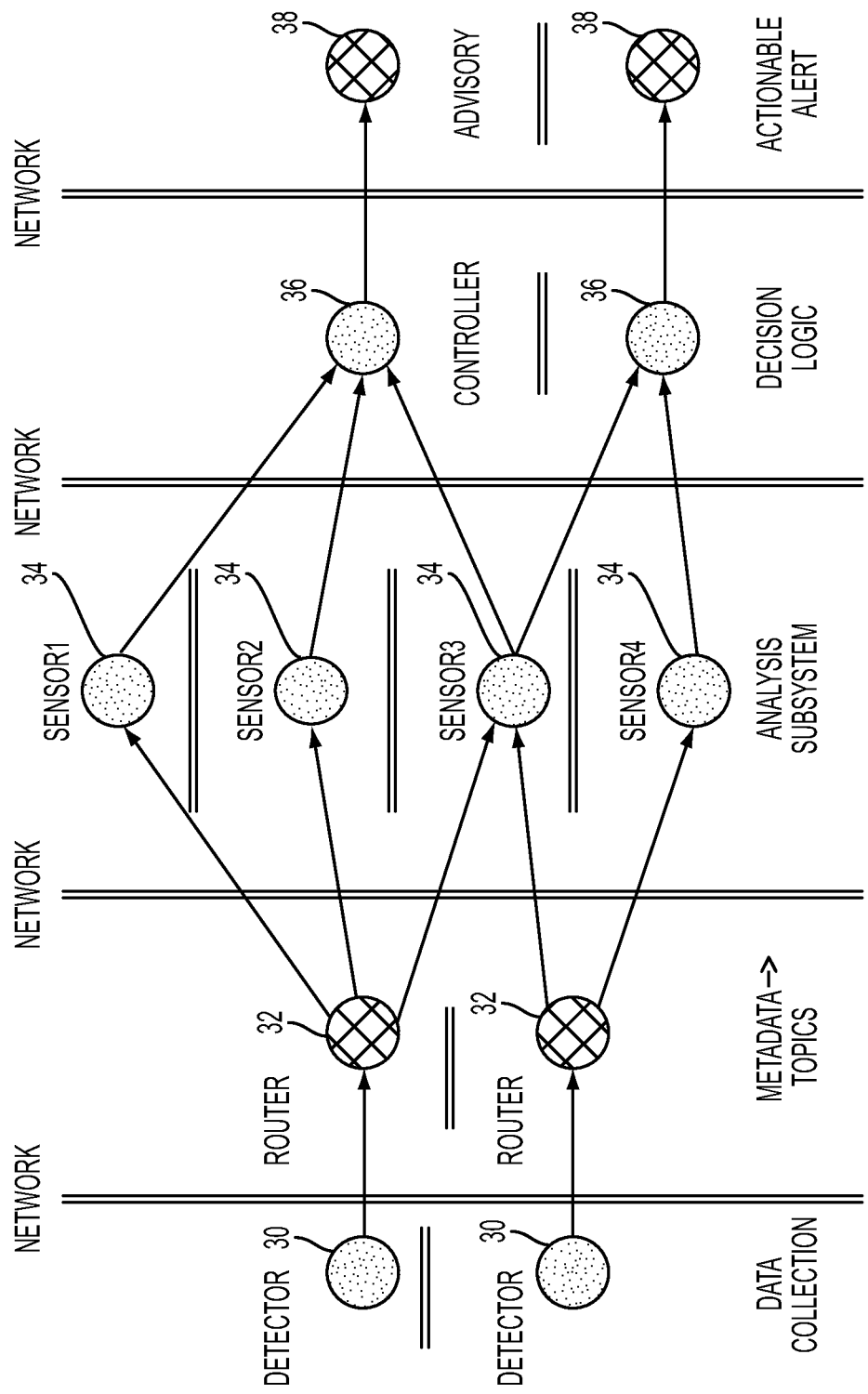
FIG. 3 illustrates a runtime view of the BioSITES System in one embodiment of the present invention.

FIG. 3 shows the BioSITES Kernel which is achieved by connecting software components (the circles in the figure)

from multiple institutions. These software components are connected via the message oriented middleware (MOM) ActiveMQ. MOM uses the publish-subscribe pattern to connect software components. Data is forwarded from one component to another when the second component subscribes to the first. In the embodiment shown in FIG. 3, BioSITES components include detectors 30, e.g. DNA sequencers and web crawlers, Routers 32, e.g., components that route data appropriately in the system based on the metadata, Sensors 34, e.g., analysis routines or workflows that identify and filter important signals in the data stream, Controllers 36, e.g., extensions of the Semantic Web that contain decision logic to process and integrate workflow outputs, and Advisories 38, e.g., components that contain reporting capabilities for displaying and relaying information. The double lines in FIG. 3 illustrate network boundaries. Data storage and access in the system is constrained by these network boundaries. Each component of the system is aware of all upstream components through messages that flow through the system.

A scenario begins as a free text document. An expert constructs a scenario, integrating the sensitivity and specificity of each data source. This results in an integration of information that is not misleading to users. Elements in scenario documents map directly to software components used in the BioSITES streaming kernel. Each scenario document corresponds one-to-one with a BioSITES controller 36 responsible for generating advisories related to that scenario. The controller 36 is a state machine that when it finds all of the conditions required (published by sensor algorithms) in the scenario, the controller 36 publishes an advisory and integrates information into the BioSITES data store 22 (FIG. 2).

Molecular biology is very complex and it is difficult to cover every possibility. Simple scenarios give us a starting point and basic capabilities. These capabilities can be leveraged later to discover trends and patterns present in multiple scenarios.

The BioSITES Data Store

Figure 4:
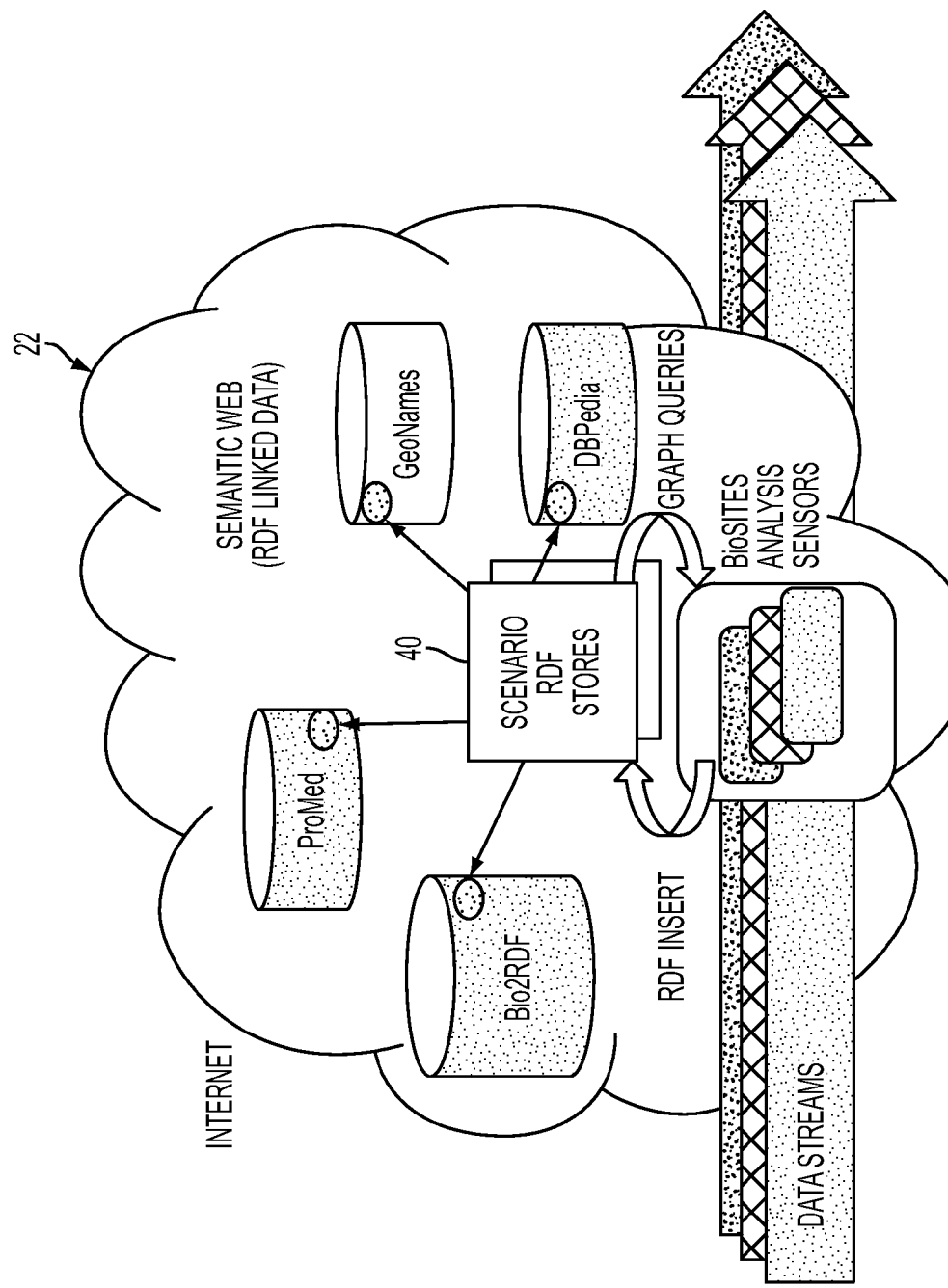
FIG. 4 illustrates a conceptual view of where data is stored in the BioSITES Data Store in one embodiment of the present invention.

The BioSITES Data Store shown in FIG. 4 combines data that exists inside the Semantic Web and data available on the Internet. In one embodiment, data in streams is analysed in near real time and is not stored. RDF Statements found on the Semantic Web are each stored in repositories owned by each institution. Portions of these repositories may also be cached in the Scenario RDF Stores 40 to improve performance. RDF Statements created by analysis are stored in RDF Stores distributed across the BioSITES system, with each store corresponding to one or a few scenarios. Catalogs required by a scenario, e.g. a set of sequences, are converted to RDF, and then made available for traversal by software.

Data available on the Internet is handled as data streams that flow through BioSITES analysis routines (or BioSITES Sensors). These analysis routines compare a reference catalog to data found in the stream. If a match is found, the information is forwarded by the BioSITES Sensor to the controller. The controller can then choose to integrate the structured information delivered by the sensor into a local RDF model that represents a current understanding of events, genetic elements, places, people and other variables. This RDF model can be connected, via links, to other resources on the Semantic Web, so that when other information is deposited, the RDF model improves.

Example of SDDM Applied to a Global Health Threat

This section provides a demonstration of the SDDM approach, by building a multi-relational directed graph about the NDM-1 gene that confers antibiotic resistance to some of the most powerful antibiotics and is an emerging global health threat. A scenario was constructed based on the publication by Kumarasamy et al., "Emergence of a new antibiotic resistance mechanism in India, Pakistan, and the UK: a molecular, biological, and epidemiological study".

SDDM Step 1: Select a Scenario for Refinement.

A scenario is selected for refinement based on a topic of NDM-1. In particular, Kumarasamy et al. is analyzed and specifics are added about the genetics of NDM-1 (based on searches of NCBI and ProMed), times when NDM-1 has appeared, and geo-locations where NDM-1 has appeared, to construct the following scenario:

Antibiotic Resistance Gene NDM-1 Located on Gram Negative Plasmid

Gram-negative *Enterobacteriaceae* with resistance to carbapenem conferred by New Delhi metallo-β-lactamase 1 (NDM-1) is a public health threat. "Resistance to beta-lactam antibiotics has become a particular problem in recent decades, as strains of bacteria that produce extended-spectrum beta-lactamases have become more common. These beta-lactamase enzymes make many, if not all, of the penicillin and cephalosporin ineffective as therapy. Extended-spectrum beta-lactamase-producing *E. coli* are highly resistant to an array of antibiotics and infections by these strains are difficult to treat. In many instances, only two oral antibiotics and a very limited group of intravenous antibiotics remain effective. In 2009, a gene called New Delhi metallo-beta-lactamase (shortened NDM-1) that even gives resistance to intravenous antibiotic carbapenem, were discovered in India and Pakistan in *E. coli* bacteria. NDM-1 is known to exist on a plasmid and has been transferred across bacteria via horizontal gene transfer.

Increased concern about the prevalence of this form of "superbug" in the United Kingdom has led to calls for further monitoring and a UK-wide strategy to deal with infections and the deaths. Susceptibility testing should guide treatment in all infections in which the organism can be isolated for culture."

In addition, BioSITES detectors are determined as follows:

BioSITES Detector 1 (data source 1): First responders/clinicians isolate the laboratory strain using the techniques outlined in the CDC manual. When the patients remain ill, the samples are sequenced with a 454 pyrosequencer. geo-location of where the sample was obtained is imbedded in metadata accompanying the sample. Note, this includes all 454 runs taken from the sick, not just *E. coli* infections.

BioSITES Detector 2 (data source 2): As new ProMed articles are published, software serializes the articles and streams them through the BioSITES Kernel. Note these articles may not relate to NDM-1.

Further, BioSITES reference data is determined as follows:

BioSITES Data Catalog_1 (reference data): Three representative sequences were found at NCBI with GI numbers: 300422615, 255031061 and 302826879.

BioSITES Data Catalog_2 (reference data): Occurrence of NDM-1 can be found in historical ProMed articles: 20100815.152812, 20100817.2853, 20100914.3325, 20101005.3604, and 20101028.3908.

Next, BioSITES analytical techniques are determined as follows:

BioSITES Sensor Method_1 (analytical technique 1): A nucleotide level BLAST (at significance level 1e−15) for detecting a match between CATALOG_1 and the sequence reads from DETECTOR 1. The blast alignment must match the region of the sequence corresponding to the NDM-1 gene.

BioSITES Sensor Method_2 (analytical technique 2): GPS coordinates are obtained for the source location of the sample and imbedded in the metadata of read sets from sequencing machines. Each sample obtained will be scanned to identify a match to positions in CATALOG1003_2. If the GPS coordinates do not match coordinates in the existing catalog, then this indicates a possible new location where NDM-1 has spread.

BioSITES Sensor Method_3 (analytical technique 3): ProMED mail articles are scanned using Data Catalog_2 for additional content relating to NDM-1.

SDDM Step 2: Create First Iteration of RDF Multi-Relational Directed Graph.

Figure 5:
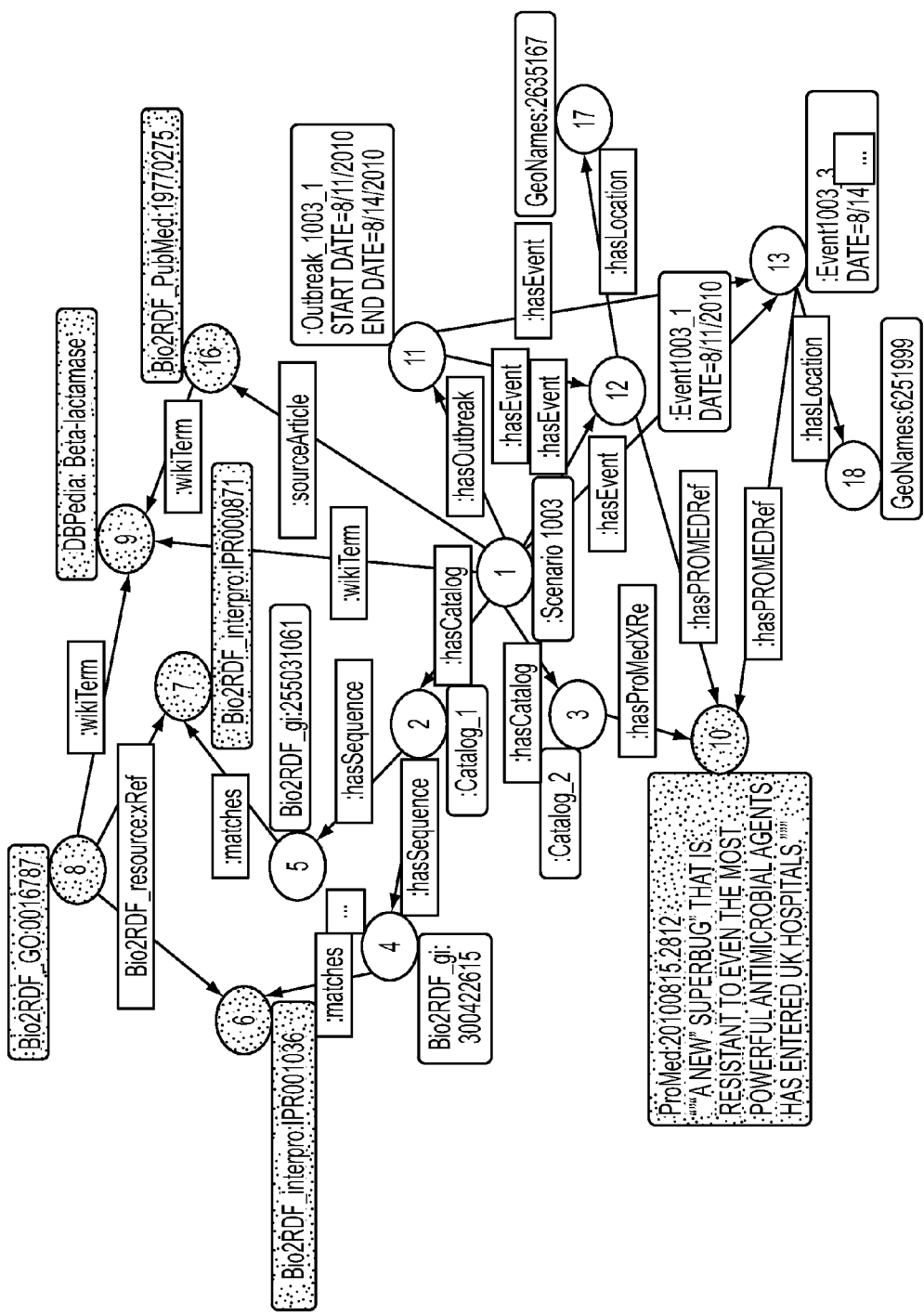
FIG. 5 illustrates a simplified view of the results from the SDDM process in one embodiment of the present invention.

Step 2 of the SDDM process focuses on conversion of the scenario into a multi-relational directed graph, as shown in FIG. 5. To convert the scenario into a MRDG, BioSITES scenario ontology and Protégé are used to re-write the scenario into a RDF/XML document. Creation of the RDF graph begins with a single node, representing the BioSITES scenario document (FIG. 5, node 1). As shown in FIG. 5, five different ontologies are used in the construction of this multi-relationship graph: the Scenario Ontology (abbreviated with a colon, :), Bio2RDF (abbreviated with Bio2RDF_X where X is a namespace tag e.g. if X=PubMed, then Bio2RDF_PubMed=http://bio2rdf.org/pubmed), GeoNames, ProMed, and DBPedia. The SDDM process creates all edges in the example, and all nodes in black and white. Bio2RDF (Blue), GeoNames (Green), and DBPedia (Purple) nodes already exist on the Semantic Web. Red nodes representing ProMed mail articles are integrated using an RDFizer as part of the SDDM process.

The NDM-1 example created RDF individuals corresponding to Wikipedia articles, InterProScan models, PubMed articles, ProMed articles, Gene Ontology terms, a scenario, catalogs, events, outbreaks, NCBI sequences (gi numbers), and GeoName locations. The nodes and edges diagrammed in FIG. 5 are physically stored in five locations: Bio2RDF nodes marked in blue are stored on the main Bio2RDF server or an acceptable mirror, GeoNames nodes marked in green are stored on the GeoNames infrastructure, DBPedia nodes marked in purple are stored on the DBPedia servers or a mirror, ProMed nodes marked in red are stored in a local graph database (Neo4j), and nodes and relations identified in the scenario, marked in black, are stored in a local RDF database on the machine where the scenario is built.

RDF statements then connect the BioSITES scenario to resources on the Semantic Web. This example scenario is based on the PubMed article 19770275, so the Scenario:sourceArticle property was used to connect the scenario object to the Bio2RDF_pubmed:19770275 article, shown as node 16 in FIG. 5. This indirectly links MESH terms, GO terms, PubMed articles and similar entities already connected via the Bio2RDF project. These terms and articles can be used to find scenarios that are related.

This multi-relational directed graph is not a static entity. Instead, as more information is identified, the graph is updated (See step 3, 4 and 5). The multi-relational directed graph links resources already on the Semantic Web into a data structure that is used by BioSITES sensors. The result at this stage is a minimal graph in that it only represents what was included in the scenario with direct links to external resources on the Semantic Web. The multi-relational directed graph constructed in this step of the SDDM process links location (GeoNames), Dates (scenario:events), and molecular objects (Bio2RDF resources).

SDDM Step 3: Identify Resources Required by the Scenario but Absent in the Semantic Web and Convert the Resources to RDF.

The construction of the two catalogs described in the scenario, NDM-1 genes and ProMed articles related to NDM-1 (Catalog_1 and Catalog_2 respectively), illustrates two common situations. The first situation links elements in the scenario document to elements that already exist (or will soon exist via a third party update) in the Semantic Web using RDF statements. The second situation involves creating new Semantic Web content by RDFizing data represented in traditional structures and then linking the scenario document elements to the newly created Semantic Web content.

In this example, a search was used to identify examples of the NDM-1 gene. One version of Bio2RDF did not contain annotated sequences for the GI numbers outlined in the scenario. This required the construction of Bio2RDF entries for each of the sequences identified in the scenario. The Bio2RDF software suite was used for the conversion. An RDF catalog (FIG. 5 node 2) was created to link the scenario object to each known instance of the NDM-1 gene (FIG. 5 nodes 4,5, . . . ). InterProScan was used to connect each Bio2RDF_gi instance linked by Catalog_1 to functional annotation on the Semantic Web (FIG. 5 nodes 6,7,8, . . . ). Functional annotation properties include gene ontology terms, HMMer profiles, and scientific terms. This functional annotation connects entities identified in this scenario to catalogs used in other scenarios that have similar functional annotation. In one embodiment, this will help generalize scenarios and automatically generate them. For example, NDM-1 is annotated as a Beta-lactamase, which based on sequence similarity, matches several entries in the MvirDB database. MvirDB is applicable in many scenarios involving category A agents.

A second catalog, data source 2, (FIG. 5, node 3), has been constructed to represent historical articles from ProMed. An RDFizer was constructed to convert historical ProMed articles into RDF. For each article, information, e.g., the article ID, date, subject line and text, were extracted and a simple RDF graph was populated. ProMed articles referencing NDM-1 were mined to identify the time and location of NDM-1 events. When the technology to reliably extract locations from the articles and associate them with events is not available, manual extraction of the locations for those articles relating to NDM-1 is required.

Three rdfs:classes were used in construction of the multi-relational directed graph representation for the disease spread described in ProMed; Scenario:event, Scenario:outbreak, and GeoNames:Feature. These rdfs:classes correspond to time (Scenario:event), time intervals (Scenario:outbreak), and geo-location (GeoNames:Feature/GeoNames:Location). A Scenario:event describes a real world event as it is described in ProMed. Data associated with this event (e.g. the time and date) are embedded as rdfs:Literals and associated with the event object. Concepts described in the event such as symptoms, locations, genetic sequences and other articles are described by Resource Description Framework Schema (RDFS) statements that link the Scenario:event to rdfs:Resources on the Semantic Web.

FIG. 5 illustrates how events are linked to locations, using the rdfs statement <Scenario:Event1003_1 Scenario:hasLocation GeoNames:2635167>. GeoNames:2635167 represents the United Kingdom. GeoNames maintains synonyms for this location, GPS coordinates, elevation, population, and other geographic specific information. Scenario:outbreaks are used to connect sets of Scenario:events. A Scenario:outbreak contains events that co-occur in time and have an occurrence of a disease/infection greater than would be expected in an area. Scenario:outbreak objects are used in the system to model disease spread over time and associate disease spread with genetic variation. FIG. 5 shows a simplified version of the multi-relational directed graph constructed as a result of steps 2 and 3 of SDDM process.

SDDM Step 4: Identify Data Feeds.

This step of the SDDM process may primarily focus on the identification of data sources (often near-real time data streams). In the NDM-1 scenario, we identified the Sequence Read Archive at NCBI (http://www.ncbi.nlm.nih.gov/sra) as a source of genetic information (serving as a proxy for high throughput sequence data), and ProMed mail as a source for geo-location and time based information. For the sequence data, we implemented a BioSITES detector that monitors NCBI Entrez for new or updated submissions to the Sequence Read Archive (SRA). If a new or updated submission is detected, reads from the submission are streamed across the network to every computer running a sensor that subscribes to the SRA BioSITES detector. A program to automatically download new ProMed articles as they are published and stream them through the BioSITES kernel was developed. Articles in the ProMed data stream are not automatically converted to RDF in the streaming process. However, if a new article matches a catalog in the BioSITES system (i.e. if the ProMed article has content relating to NDM-1), then relevant elements of the article are extracted and represented in RDF. This process, although subjected to some automation, was mostly a manual effort.

SDDM Step 5: Identify Analytical Routines for Comparing Information in the Data Stream to the Concepts Outlined in the Scenario.

Scenarios require the use of one or more sensors to analyze streams of data coming from detectors. In the NDM-1 scenario, the sensor (Sensor_1) was defined to compare sequences in a data stream to the NDM-1 catalog (Catalog_1) based on alignment. In this case, we used the BioSITES BLAST sensor to match reads in the read set to sequences in Catalog_1 (e value −15). When a read set matches a sequence in Catalog_1, RDF statements describing the match can be added to the multi-relational directed graph (FIG. 6).

Figure 6:
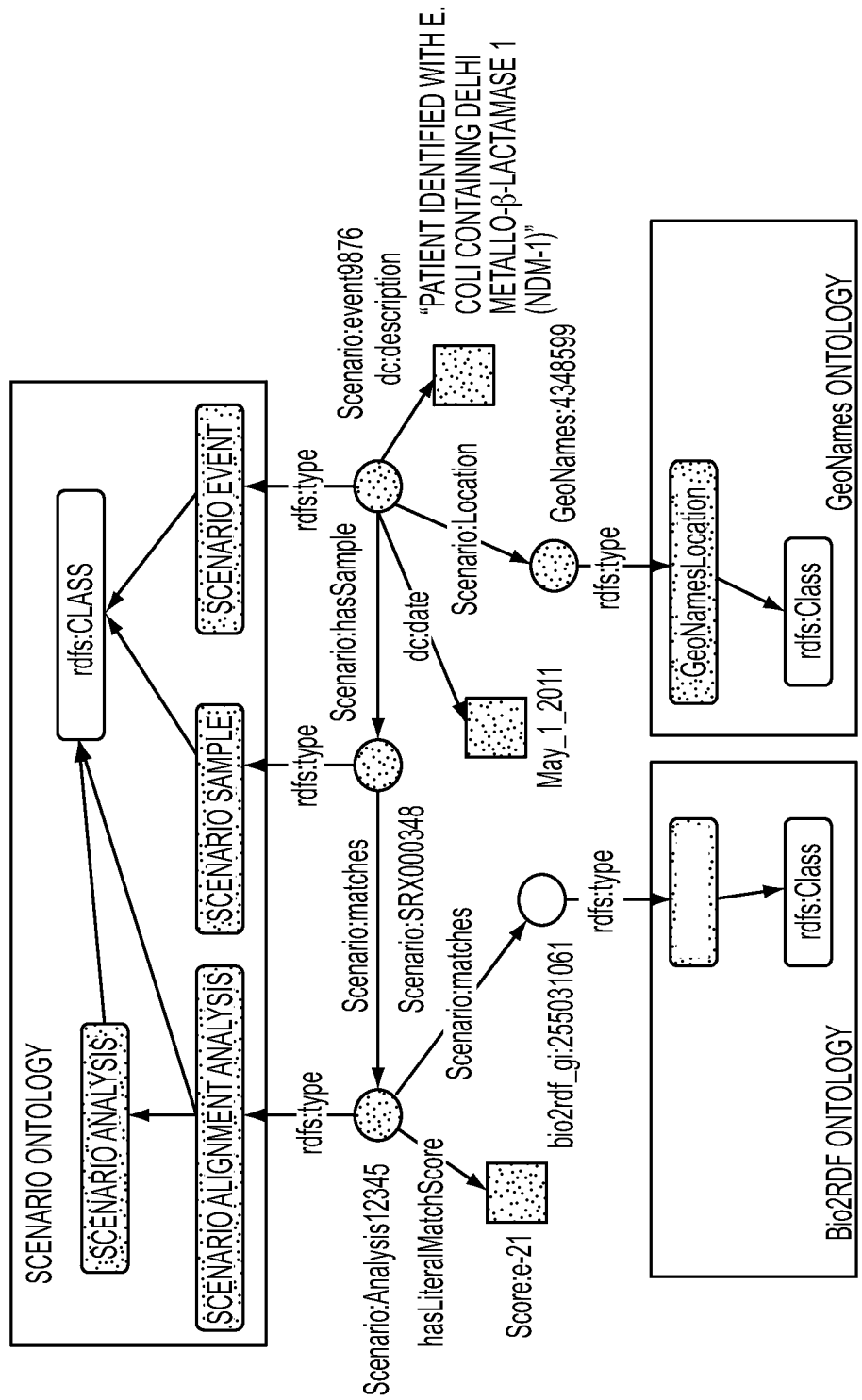
FIG. 6 illustrates a multi-relational multi-ontology directed graph representing the output from an analytical routine (BioSITES sensor) in one embodiment of the present invention.

As shown in FIG. 6, RDF Statements represent the results from an analysis (statements are each edge shown in blue). Statements are also made between entities of the multi-relational directed graph, Literals (blue squares) and ontologies (Scenario, bio2rdf, and GeoNames). Ontologies (dashed rectangles) also contain relationships between classes (rounded rectangles). An analysis is responsible for linking bio2rdf entities to samples. Samples correspond to events and events have locations.

The NDM-1 scenario also required the construction of an additional sensor (Sensor_2) to compare global positions and text in ProMed articles (Catalog_2). Newly published ProMed articles are scanned to identify Delhi metallo-β-lactamase 1 (NDM-1) or close synonyms. If the article matches, it is then scanned for location matches in the GeoNames database. All matches are geo-coded and associated with one or more new events. This information is serialized to the NDM-1 controller where it is converted into RDF.

SDDM Step 6: Based on the Scenario and the Resulting MRDG, Identify the Data Outputs that Meet End-User Decision Support Needs and Define Queries to Produce Those Outputs.

In this step, the SDDM process may use the scenario derived data model as a query-able resource of decision support information for consumption by an end-user. In the NDM-1 scenario, the following questions can now be answered by querying the data model:

When did the NDM-1 events occur?

In what locations around the globe did NDM-1 occur?

What genetic variation in the NDM-1 gene was found?

Each of these questions can be answered by traversing the multi-relational directed graph starting at the scenario node. For example, to find the dates of all NDM-1 events, first follow the outgoing edges from Scenario:Scenario1003. If the node reached is of type Scenario: event, then report the date property. Otherwise, if it is of type outbreak, follow all outgoing edges to reach nodes of type Scenario:event and report their date (e.g., depth first search). Graph based traversals can be easily extended to support queries to find geo-location and genetic variation information on this NDM-1 data model. More complex queries are also possible using path algebra. Sensors continuously deposit more RDF statements into the multi-relational directed graph as they analyze data streams. As the multi-relational directed graph gets updated, the traversal behaviour and results may change. This forms the basis for user interfaces.

Traversing the Generated Model.

From a technical perspective, traversing the model generated by SDDM may include constructing programs that crawl the linked data on the Semantic Web. Here we will illustrate how these programs can be constructed using the Gremlin programming language. Gremlin is a scripting language optimized for traversing graph structures, much the same way a person may navigate the web. Gremlin is built on top of the Groovy programming language which itself is built on top of Java. Java code and Groovy code will both work inside of Gremlin. Gremlin itself sits in a technology stack for interacting with graph databases that includes Pipes, Blueprints, Rexter, and many graph databases including Neo4J, OrientDB, DEX, and RDF Sail graphs. Gremlin is similar to SPARQL, it is a language for expressing queries over multi-relational graphs. Gremlin is functionally superior to SPARQL, but lacks the intuitive and simple syntax. Both Gremlin and SPARQL can be imbedded into software written in Java. Here we will limit the discussion of the Gremlin features to those queries alluded to in the previous section.

The first query considered in the previous section is: when did the NDM-1 events occur? The following Gremlin code loads the scenario RDF model into memory, adds namespaces to increase usability and readability, seeds the start of the query at the Scenario1003 node (Node 1 in FIG. 5) and then traverses the model. The traversal starts at node 1 (represented as v in the script). The statement v.out(BioSITES:hasOutbreak) retrieves all of the nodes of type BioSITES:outbreak reachable from v. A statement of type v.out( ) gets the URI of the node, a statement of type v.outE( ) gets outgoing edges from v. These statements can be chained together to complete a query. An example of such a traversal is shown below.

```
          \,,,/
          (o o)
-----oOOo-(_)-oOOo-----
gremlin> g = new MemoryStoreSailGraph( ) //create an in memory Sail graph
//load the triples from a single scenario into the graph
gremlin> g.loadRDF(new FileInputStream('NDM1.ntripple'),
'http://www.biosites.org/Scenario1003.n3#', 'n-triples', null)
==>sailgraph[memorystore]
//add namespaces to increase readability
gremlin> g.addNamespace('bio2RDF_interpro', 'http://bio2rdf.org/interpro:')
gremlin>
g.addNamespace('scenario','http://www.compbio.ornl.gov/ontology/scenario.owl#')
gremlin> g.addNamespace('dc','http://purl.org/dc/elements/1.1/')
gremlin> g.addNamespace('BioSITES', 'http://www.biosites.org/Scenario1003.n3#')
gremlin> g.addNamespace('dbpedia', 'http://dbpedia.org/resource/')
//navigate/seed to the 'scenario' node at the center of the graph.
gremlin> v = g.v('BioSITES:Scenario1003')
==>v[http://www.biosites.org/Scenario1003.n3#Scenario1003]
//When did the NDM-1 events occur?
gremlin> v.out('BioSITES:hasOutbreak').out('scenario:hasEvent').outE('dc:date')
==>e[BioSITES:Event1003_3 - dc:date -> "2010-8-13"^^<xsd:date>]
==>e[BioSITES:Event1003_5 - dc:date -> "2010-8-16"^^<xsd:date>]
==>e[BioSITES:Event1003_4 - dc:date -> "2010-8-14"^^<xsd:date>]
==>e[BioSITES:Event1003_6 - dc:date -> "2010-8-16"^^<xsd:date>]
==>e[BioSITES:Event1003_10 - dc:date -> "2010-6-11"^^<xsd:date>]
==>e[BioSITES:Event1003_9 - dc:date -> "2010-03-11"^^<xsd:date>]
==>e[BioSITES:Event1003_8 - dc:date -> "2010-07-01"^^<xsd:date>]
==>e[BioSITES:Event1003_11 - dc:date -> "2010-21-10"^^<xsd:date>]
==>e[BioSITES:Event1003_12 - dc:date -> "2010-9-13"^^<xsd:date>]
==>e[BioSITES:Event1003_13 - dc:date -> "2010-9-13"^^<xsd:date>]
==>e[BioSITES:Event1003_14 - dc:date -> "2010-8-11"^^<xsd:date>]
==>e[BioSITES:Event1003_7 - dc:date -> "2010-9-11"^^<xsd:date>]
==>e[BioSITES:Event1003_15 - dc:date -> "2010-04-10"^^<xsd:date>]
==>e[BioSITES:Event1003_2 - dc:date -> "2010-8-12"^^<xsd:date>]
==>e[BioSITES:Event1003_1 - dc:date -> "2010-8-11"^^<xsd:date>]
```

Note, that the Semantic Web may be traversed using the same techniques. For example to traverse the Bio2RDF repository from 'bio2rdf_interpro:IPR001036', do:

The added .value asks Gremlin to display only the values on the property nodes and not the URI. This is also applied above to get the value for dates.

```
gremlin> g = new LinkedDataSailGraph(new MemoryStoreSailGraph( ))
==>sailgraph[linkeddatasail]
gremlin> g.v('http://bio2rdf.org/interpro:IPR001036').outE( )
==>e[bio2RDF_interpro:IPR001036 - http://fortytwo.net/2008/01/webclosure#memo ->
"status=Success; timestamp=2011-07-
04T20:10:06"]<http://fortytwo.net/2008/01/webclosure#context>
==>e[bio2RDF_interpro:IPR001036 - http://bio2rdf.org/bio2rdf_resource:url ->
"http://bio2rdf.org/"]<bio2RDF_interpro:IPR001036>
==>e[bio2RDF_interpro:IPR001036 - http://bio2rdf.org/bio2rdf_resource:url ->
"http://bio2rdf.org/html/interpro:IPR001036"]<bio2RDF_interpro:IPR001036>
==>e[bio2RDF_interpro:IPR001036 - rdfs:label ->
"[interpro:ipr001036]"]<bio2RDF_interpro:IPR001036>
==>e[bio2RDF_interpro:IPR001036 - http://bio2rdf.org/bio2rdf_resource:lsid ->
urn:lsid:bio2rdf.org:interpro:ipr001036]<bio2RDF_interpro:IPR001036>
==>e[bio2RDF_interpro:IPR001036 - owl:sameAs ->
http://bio2rdf.org/interpro_resource:IPR001036]<bio2RDF_interpro:IPR001036>
==>e[bio2RDF_interpro:IPR001036 - rdf:type ->
http://bio2rdf.org/interpro_resource:Annotation]<bio2RDF_interpro:IPR001036>
```

This allows programs to update information when the local copy gets out of sync with the copy at Bio2RDF.

The second question, 'in what locations around the globe did NDM-1 occur?' is answered by a very similar traversal.

```
//In what locations around the globe did NDM-1 occur?
gremlin>
v.out('BioSITES:hasOutbreak').out('scenario:hasEvent').out('scenario:hasCoordinates').
value
==>4.790039,50.359482,0.000000
==>72.875061,19.014086,0.000000
==>19.138184,42.924252,0.000000
==>134.208984,-25.045792,0.000000
==>117.246094,27.293690,0.000000
```

```
==>119.750977,30.486551,0.000000
==>21.972656,39.164143,0.000000
==>-48.076172,-15.623037,0.000000
==>-120.234375,36.949890,0.000000
==>-89.121094,40.513798,0.000000
==>-71.015625,42.358543,0.000000
==>139.482422,37.020100,0.000000
==>121.113281,24.287027,0.000000
==>-102.041016,55.727112,0.000000
==>-2.065430,53.330872,0.000000
gremlin>
```

To answer the question, 'what genetic variation in the NDM-1 gene was found?' we wrote the following script that traverses the graph for protein sequences, and then does a system call to the Muscle multiple sequence aligner.

There are many possibilities regarding using Gremlin to traverse graphs. As a JVM language, Gremlin has the full power and flexibility of Java and Groovy to implement graph traversal algorithms. These algorithms can manipulate mul-

```
import java.io.*; //allow system calls
//setup a file for writing
def fastaFile = new BufferedWriter(new FileWriter("tmp.fasta"))
//Start Traversing
v.out('scenario:hasCatalog').out('scenario:hasNCBIXREF').out('scenario:hasProteinSeque
nce'){fastaFile.write(">\n" + it.value + "\n")} >>-1
fastaFile.close( )
println "Running Muscle multiple sequence aligner..."
def p = Runtime.getRuntime( ).exec("./muscle -clw -in tmp.fasta")
def stdInput = new BufferedReader(new InputStreamReader(p.getInputStream( )))
def stdError = new BufferedReader(new InputStreamReader(p.getErrorStream( )))
while ((s = stdInput.readLine( )) != null) { println s }
```

The output of this traversal is as follows:

```
> ./gremlin.sh -e rdf2msa.grm

Starting Traversal . . .

Running Muscle multiple sequence aligner . . .

MUSCLE (3.8) multiple sequence alignment

------------------------------------------------------------
MELPNIMHPVAKLSTALAAALMLSGCMPGEIRPTIGQQMETGDQRFGDLVFRQLAPNVWQ
------------------------------------------------------------

------------------------------------------------------------
HTSYLDMPGFGAVASNGLIVRDGGRVLVVDTAWTDDQTAQILNWIKQEINLPVALAVVTH
----LDMPGFGAVASNGLIVRDGGRVLVVDTAWTDDQTAQILNWIKQEINLPVALAVVTH

-----MGGMDALHAAGIATYANALSNQLAPQEGMVAAQHSLTFAANGWVEPATAPNFGPL
AHQDKMGGMDALHAAGIATYANALSNQLAPQEGMVAAQHSLTFAANGWVEPATAPNFGPL
AHQDKMGGMDALHAAGIATYANALSNQLAPQEGMVAAQHSLTFAANGWVEPATAPNFGPL
     ***********************************************

KVFYPGPGHTSDNITVGIDCSDIAFGGCLIKDSKAKSLGNLGDADTEHY-----------
KVFYPGPGHTSDNITVGIDGTDIAFGGCLIKDSKAKSLGNLGDADTEHYAASARAFGAAF
KVFYPGPGHTSDNITVGIDGTDIAFGGCLIKDSKAKSLGNLG-----------------
******************  :*******************

------------------------------
PKASMIVMSHSAPDSRAAITHTARMADKLR
------------------------------
``` tiple graphs, traverse the Semantic Web, cache important subgraphs for use as catalogs, and process data streams.

DISCUSSION

In one embodiment of the present disclosure, the SDDM process solves a very daunting challenge: to be able to detect an outbreak as early as possible and perhaps even prevent it. Early detection may require the capacity to monitor data feeds such as online medical records, detectors such as JBAIDS, doctor's blogs and social media for early indicators of an outbreak or a new disease. Prevention may require the ability to look deeper into the causative agents of the disease such as genetic components and quickly manufacture and deploy countermeasures. The capacity to do both these well is found in our ability to consume a massive amount of data as it is produced in real time, in our ability to integrate multiple sources of information of widely different types and our ability to understand the limitations and potentials of each data source.

While the inventive system can be quite robust, the simple example presented here falls short of completely addressing this grand challenge in several respects. First, there is increasing evidence that the mainstream media (covered in the example via ProMED) can be quite slow to respond to an outbreak. For example, in the recent E. coli scare in Germany, ProMED sent its first alert on May 24, 2011; however, the first cases occurred nearly a month earlier. Other sources of information are possibly better suited to early detection than ProMED and the mainstream media. While genetic sequencing has begun to be used as a diagnostic tool, it is not currently easily accessible globally. However, unlike PCR, sequencing will not miss subtleties such as signatures of genetic engineering or novel horizontally transferred genes. So, recognizing that they are not perfect, we chose these two feeds in our SDDM example because they represent very different data types, and therefore have different properties. From a technical perspective, a demonstrated capability to integrate data as divergent as free text and DNA sequence makes integration of more structured information such as medical records, output from diagnostic tools, and over the counter sales possible.

These data sources are not representative of all that may be needed or used in bio-surveillance, they are just two examples. Different or additional data feed may be utilized. The bio-surveillance may be performed by simultaneous integration of a plurality, or tens or perhaps even hundreds of data feeds. SDDM in one embodiment is a technique that integrates multiple sources of information, each with different advantages, resolutions, timeliness, and capabilities. SDDM benefits from RDF as a robust and flexible data model for representing information of different types. RDF can effectively represent geographic positions, events, timelines, genetic features, people, social networks, publications, and even concepts extracted from free text. Another RDF advantage is that researchers in different fields can cooperate and build extremely complex models. SDDM takes advantage of these models using DBpedia, GeoNames, Bio2RDF, and other ontologies and resources on the Semantic Web.

A second attribute of SDDM is that algorithms, processing methods and analytic routines can be custom built. This allows the scenario writer to focus on the needs outlined in the scenario instead of building general purpose software that is overly complex and not based on meeting objectives. SDDM uses the idea of a scenario to reduce complexity. The scenario describes, in concrete terms, the goal of the integration. Elements outside of this goal may be ignored. For example, to be viewed as a success, a scenario driven integration need only meet the requirements specified in the scenario. It may be up to the broader community to determine if the scenario meets its needs.

The use of scenarios is that they may help model past events. A library of known threats may also provide the capability to generalize. It may be possible to connect scenarios in unforeseen ways and thus build software that is broadly applicable. This is possible because causative agents will exist in the RDF graph (e.g., a toxin). A simple way to connect two scenarios is through a causative agent they both share (e.g., scenario A and B share the same toxin). Shortest path algorithms are one way to find if two elements are related in a graph. If two elements are related, then software can be generalized to detect both elements.

Materials and Methods

Application of SDDM to the NDM-1 example produces a scenario with detectors, catalogs, and sensors for the BioSITES system. Here elements of BioSITES are further described to provide context for how a scenario derived from SDDM may be processed.

Example Software and Techniques Used in the Streaming Data Kernel

Each component of the Streaming Data Kernel was coded in Java. Each component or program continually runs; when it receives a new message, it processes the message and then may send messages to other software components. ActiveMQ was used to connect each of the following BioSITES software components: Detectors, Sensors, Routers, and Controllers. Software component A is connected to software component B using publish-subscribe. Briefly, ActiveMQ implements publish-subscribe through the use of a broker. Brokers run continuously. They can run on the same machine as the program that wishes to send messages, on the same machine where the program receiving messages resides or on a totally different machine. Programs that wish to send messages, send them to the broker using the ActiveMQ API. Programs that wish to receive messages connect to the broker and notify it that they wish to receive all messages sent by a particular program. ActiveMQ is a messaging protocol that allows components to be coded in many languages, including C++, .NET, Perl, Java, Python and Ruby.

Additional languages and technology were also used in the construction of the streaming data kernel, mainly due to programmer choice. The sequence read archive detector was written in Perl. It queries Entrez on a regular schedule (currently every 24 hours—but this is variable) to find new submissions. When a new submission is found, it downloads the data and metadata (stored in XML) for each submission. The Perl program then calls a Java executable that uses JAXB (Table 2) to parse the contents of the XML-metadata into java objects, place the content of these objects into a message, contact the broker, and forward a message to downstream routers. This message also contains a URI corresponding to a local location where the raw sequence data is stored. Routers pick up this message and examine the metadata of the message and forward the message to sensors interested in reads of a specific type. The sequence read archive for example currently contains 'Whole Genome Sequencing', 'Metagenomics', 'Transcriptome Analysis', 'Resequencing', 'Synthetic Genomes', 'Forensic or Paleo-genomics', 'Gene Regulation Study', 'Cancer Genomics', 'Population Genomics', 'RNASeq', and 'Other'.

Sensors or analysis algorithms will only be interested in a subset of these study types, so they will subscribe only to those studies of interest through the ActiveMQ broker running on the routing machine. Sensors receive the message, download the raw sequence data, and begin computational analysis on it. In the case of the NDM-1 Blast sensor, the sensor has a copy of the NDM-1 sequences. When it receives a message that new sequences are available, it downloads a subset of the data, performs a system call to format the blast database on the new sequences, and then performs another system call to run Blast for all of the NDM-1 sequences against the newly formatted blast database. It then parses the output, and if there is a match, publishes the match to an outgoing ActiveMQ queue. Controllers that will render the advisory then consume this message. The NDM-1 sensor updates its copy of the NDM-1 sequences periodically by connecting to the server that contains the NDM-1 scenario through an ActiveMQ broker. When the server that contains the scenario receives the request, it performs a query to find all sequences on the server related to the NDM-1 catalog, and then sends the updated sequences back to the NDM-1 sensor in fasta format. A similar method is used when the sensor has found a new NDM-1 gene and would like to add it to the catalog on the scenario server.

The ProMED data stream was constructed using the Groovy programming language. This program periodically looks at the sequential ID's generated by the ProMED mail website when a new article is published. The ProMED mail detector forwards the article via an ActiveMQ broker where it is picked up by the ProMED NDM-1 sensor. This sensor has a copy of all ProMED mail articles relating to NDM-1. Currently, it does a pattern match on the incoming article to determine if it is similar to the NDM-1 articles in the reference catalog. If a match is found, it forwards an RDFized version of the article to the NDM-1 scenario server where it is added to the catalog. This includes parsing the title, date, ProMED ID and content into RDF statements. In one embodiment, it might not infer structure about entities in the article and create RDF statements from raw text.

Example Hardware Used

The BioSITES kernel in one embodiment can be run on a Linux system with 68 compute nodes, a management node, a backup management node and a data staging storage system. Each compute node has dual AMD Opteron 6134, 2.3 GHz processors (8 cores/CPU, 16 cores/node, 1088 cores/cluster). Each compute node has 64 GB DDR3 1333 MHz registered ECC memory (4 GB/core, 4.4 TB/cluster) and 4×2 TB disk drives (8 TB/node, 544 TB/cluster). Data staging storage with 36 TB RAID array. Local storage on the nodes is currently 62% allocated, mostly by short read data and web data on the Hadoop filesystem. This system currently runs 2000 concurrent analysis algorithms or BioSITES 'sensors'. These sensors have various functions, but a majority perform sequence analysis. The system also currently runs up to 64 concurrent 'detectors' that stream data for analysis to the BioSITES system. A single server in the same class as each node in the cluster is used to store our Bio2RDF mirror. Each running controllers are also running on the same hardware, one controller per instantiated scenario (e.g. the NDM-1 example outlined here has one running controller for serving RDF).

As an example, to contribute a scenario, or to add additional elements to the multi-relational graph as it is refined, a knowledgeable user need only use a personal computer and the Protégé software. Protégé can import external resources such as ontologies given they are of manageable size.

Example Software and Techniques Used in the Semantic Catalogs

An RDF catalog may be similar to HTML. RDF can be stored on files in the filesystem and then served by a web server like HTML content. For advanced queries, RDF can also be stored in a graph database. Examples include OrientDB, Neo4J, DEX, Jena's TDB, AllegroGraph and Virtuoso (see Table 2). Graph database queries are executed in SPARQL or Gremlin depending on the database. Bio2RDF consumes about 2 TB in size for a complete mirror, and each shard of the database is stored in a Virtuoso instance. Neo4J was used to import the ProMED mail archive for easy searching.

In the case of NDM-1, the scenario object was copied from the ontology editing computer and RDF triples were imported into a Neo4J sail store for access over Rexter. This allows a very small scenario model (i.e. about 80K) to interoperate seamlessly with Bio2RDF, GeoNames, and DBPedia infrastructures. Each of these resources provides SPARQL endpoints for querying and HTTP access for navigation. Graph traversals are implemented in Gremlin. Other implementations are possible.

The SDDM process in one embodiment uses a scenario to create software and a data representation. The result is a multi-relational directed graph containing the entities and relationships between entities required for the BioSITES system. This allows the BioSITES system to perform distributed, heterogeneous data integration in a manner not otherwise possible with traditional data modeling techniques.

The example provided herein is one where SDDM was successfully applied to complex data integration challenges. This example was chosen to be relatively simple for clarity. The process created a model of the emerging NDM-1 health threat, identified and filled gaps in that model, and constructed reliable software that monitored data streams based on the scenario derived multi-relational directed graph. Because of the complexity of the problem, the SDDM process significantly reduced the software requirements phase by letting the scenario and resulting multi-relational directed graph define what is possible and hence set the scope of the user requirements. Approaches like SDDM can be very helpful to the future of data intensive, data-driven science because they automate the process of converting massive data streams into semantic graphs or computable knowledge.

GLOSSARY

Annotation—a note that is made while reading any form of text.

BioSITES—a comprehensive program to develop a secure, authoritative, predictive, and complete reference standard for biological threat mitigation that will support detection R&D and lead to near real-time bio-surveillance.

Catalog—a collection of objects from a data repository. BioSITES catalogs are constructed by making a Scenario: CatalogX node and then connecting that node to other nodes on the Semantic Web.

Data Mashup or Mashup—a purpose driven, customized data integration that facilitates question answering on a topic of interest.

Edge—the connection between two nodes in a graph is called an edge.

Event—a single incident that happens at a determinable time and location.

Graph—constructed from nodes and edges. Edges connect nodes in a graph.

Namespace—a uniform resource identifier (URI). Typically, the URI chosen for the namespace of a given extensible markup language (XML) vocabulary describes a resource under the control of the author or organization defining the vocabulary, such as a URL for the author's Web server. In RDF and OWL, namespaces are abbreviated namespace:content, where namespace is a URI prefix, and content is the ontology term or individual data item.

NDM-1—an enzyme that makes bacteria resistant to a broad range of beta-lactam antibiotics. These include the antibiotics of the carbapenem family, which are a mainstay for the treatment of antibiotic-resistant bacterial infections. The gene for NDM-1 is one member of a large gene family that encodes beta-lactamase enzymes called carbapenemases. Bacteria that produce carbapenemases are often referred to in the news media as "superbugs" because infections caused by them are difficult to treat. Such bacteria are usually susceptible only to polymyxins and tigecycline.

Node—representation of data and/or ontology classes in a graph. Edges connect nodes together in the construction of a graph.

Object—Also called an RDF individual, this is a specific instance of a data element. In multi-relational directed graphs, nodes represent objects.

Ontology—a formal representation of knowledge as a set of concepts within a domain, and the relationships between those concepts, in computer science and information science. Ontology is used to reason about the entities within a domain, and may be used to describe the domain.

Outbreak—occurrences of a disease/infection greater than would be expected in an area.

OWL—the Web Ontology Language (OWL) is a family of knowledge representation languages for authoring ontologies. The languages are characterised by formal semantics and RDF/XML-based serializations for the Semantic Web. OWL is endorsed by the World Wide Web Consortium (W3C).

Property—an 'edge' in a multi-relational directed graph that has a relationship type (i.e. a type of property).

Protégé'—a free, open source ontology editor for editing RDF, OWL and other resources on the Semantic Web.

RDF—the Resource Description Framework (RDF) is a family of World Wide Web Consortium (W3C) specifications originally designed as a metadata data model. It has come to be used as a general method for conceptual description or modelling of information that is implemented in web resources, using a variety of syntax formats.

RDFS—the Resource Description Framework Schema.

RDFizers—software that reads traditional data representations such as relational databases, text files, and data streams and converts the content into a multi-relational directed graph. RDFizers do not always perform rigorous analysis, so information can be lost in the process.

Scenario—for BioSITES, a scenario is a structured description of a malicious action or series of actions that causes harm in health, economics, or quality of life.

Semantic Web—a "web of data" that enables machines to understand the semantics, or meaning, of information on the World Wide Web.

Tables

TABLE 1

Namespaces and abbreviations used in the text

| NAME | URI | DESCRIPTION | REFERENCE |
|---|---|---|---|
| DBpedia | http://www.dbpedia.org/ | Ontology of wikipedia entries | DBpedia: A Nucleus for a Web of Open Data |
| SO [sequence ontology] | http://www.sequenceontology.org/ | Ontology of genetic sequences | The Sequence Ontology: a tool for the unification of genome annotations |
| GO [gene ontology] | http://www.geneontology.org/ | Ontology of biological information | Gene ontology: tool for the unification of biology. The Gene Ontology Consortium |
| Bio2RDF | http://bio2rdf.org/ | Converts biological info into RDF | Bio2RDF: Towards a mashup to build bioinformatics knowledge systems |
| Scenario | www.BioSITES.org/scenario | Ontology of the BioSITES terms | |
| Interpro | http://www.ebi.ac.uk/interpro/ | Database of protein sequences | InterProScan—an integration platform for the signature-recognition methods in InterPro |
| ProMed | http://www.ProMedmail.org/ | Collection of public health articles | ProMed-mail: An Early Warning System for Emerging Diseases |
| GeoNames | http://www.geonames.org/ | Database of GPS locations around the world | Interlinking Open Data on the Web |

TABLE 2

Technologies Used in the SDDM Process

| Technology Name | Download Site | Description |
|---|---|---|
| ActiveMQ | http://activemq.apache.org/ | Used to connect each of the following BioSITES software components: Detectors, Sensors, Routers, and Controllers. |
| Rexter | https://github.com/tinkerpop/rexster/wiki/ | Rexter exposes RDF over REST. |
| JAXB | http://jaxb.java.net/ | Parses the contents of the XML-metadata into java objects, place the content of these objects into a message, contact the broker, and forward a message to downstream routers. |
| Neo4J | http://neo4j.org/download/ | Used to import the ProMED mail archive for easy searching. |
| OrientDB | http://www.orientechnologies.com/orient-db.htm | A NoSQL DBMS which can store 150000 documents per second on common hardware |
| DEX | http://www.sparsity-technologies.com/dex.php | A high-performance graph database written in Java and C++ that allows the integration of multiple data sources |
| Jena's TDB | http://www.openjena.org/TDB/ | TDB is a component of Jena. It provides for large scale storage and query of RDF datasets using a pure Java engine |
| Jena | http://www.openjena.org/ | An API for the manipulation of RDF data. |
| Sesame | http://www.openrdf.org/ | An API for the manipulation of RDF |
| AllegroGraph | http://clos.org/agraph/downloads/ | A system to load, store and query RDF data. |
| Virtuoso | http://virtueso.openlinksw.com/dataspace/dav/wiki/Main/VOSDownload | Virtuoso is an innovative enterprise grade multi-model data server for agile enterprises & individuals. |
| Gremlin | https://github.com/tinkerpop/gremlin/wiki | Gremlin is a graph traversal language |
| Protege | http://protege.stanford.edu/ | A free open-source Java tool providing an extensible architecture for the creation of customized knowledge-based applications |
| Tomcat | http://tomcat.apache.org/ | Apache Tomcat is an open source software implementation of the Java Servlet and JavaServer Pages technologies. |
| SPARQL | http://www.w3.org/TR/rdf-sparql-query/ | A relational like query interface to SQL Data |

Various aspects of the present disclosure may be embodied as a program, software, or computer instructions stored in a computer or machine usable or readable storage medium, which causes the computer or machine to perform the steps of the method when executed on the computer, processor, and/or machine. A computer readable storage medium or device may include any tangible device that can store a computer code or instruction that can be read and executed by a computer or a machine. Examples of computer readable storage medium or device may include, but are not limited to, hard disk, diskette, memory devices such as random access memory (RAM), read-only memory (ROM), optical storage device, and other recording or storage media.

The system and method of the present disclosure may be implemented and run on a general-purpose computer or special-purpose computer system. The computer system may be any type of known or will be known systems and may typically include a processor, memory device, a storage device, input/output devices, internal buses, and/or a communications interface for communicating with other computer systems in conjunction with communication hardware and software, etc.

The terms "computer system" and "computer network" as may be used in the present application may include a variety of combinations of fixed and/or portable computer hardware, software, peripherals, and storage devices. The computer system may include a plurality of individual components that are networked or otherwise linked to perform collaboratively, or may include one or more stand-alone components. The hardware and software components of the computer system of the present application may include and may be included within fixed and portable devices such as desktop, laptop, server. A module may be a component of a device, software, program, or system that implements some "functionality", which can be embodied as software, hardware, firmware, electronic circuitry, or etc.

As used in the present disclosure, the singular forms "a", "an" and "the" are intended to include the plural forms as well, unless the context clearly indicates otherwise.

The components of the flowcharts and block diagrams illustrated in the figures show various embodiments of the present invention. It is noted that the functions and components need not occur in the exact order shown in the figures. Rather, unless indicated otherwise, they may occur in different order, substantially simultaneously or simultaneously. Further, one or more components or steps shown in the figures may be implemented by special purpose hardware, software or computer system or combinations thereof.

The embodiments described above are illustrative examples and it should not be construed that the present invention is limited to these particular embodiments. Thus, various changes and modifications may be effected by one skilled in the art without departing from the spirit or scope of the invention as defined in the appended claims.

What is claimed is:

1. A computer readable storage device storing a program of instructions executable by a machine to perform a method of integrating diverse sources of data and data streams, the method comprising:

selecting a scenario for refinement based on a topic, the scenario comprising a text document that describes the topic to be examined, the scenario identifying one or more downstream data users and uses that drive said refinement of the scenario;

creating a multi-relational directed graph based on the scenario;

identifying and converting resources in accordance with the scenario and updating the multi-directed graph based on the converted resources;

identifying data feeds in accordance with the scenario and updating the multi-directed graph based on the data feeds;

creating detectors operable to continuously provide data related to the topic, the detectors receiving said data from said data feeds;

identifying analytical routines that compare information in said data to the scenario and updating the multi-directed graph using the analytical routines, the analytical routines comprising sensors that subscribe to said detectors and responsive to receiving said data, perform at least one of:

comparing, based on alignment, sequences in a data stream to sequences in entities of the multi-relational directed graph, and adding one or more statements to the multi-directed graph based on finding a match;

performing analysis among the entities, literals associated with the scenario and represented as a node in the multi-directed graph and ontologies associated with the scenario and linked to the multi-directed graph, wherein one or more relationship statements are generated between two or more of an entity, a literal, and an ontology in the multi-directed graph; and linking the entities to samples corresponding to events; and identifying data outputs in accordance with the scenario at least based on one of the one or more statements and the one or more relationship statements and defining queries to produce the data outputs from the multi-directed graph, the method further comprising consuming one or more messages from one or more of the sensors indicating a match in said data, the consuming performed by a controller comprising a state machine, and the controller publishing an advisory responsive to finding that all conditions in the scenario are met based on said one or more consumed messages.

2. The computer readable storage device of claim 1, the selecting the scenario comprising:

obtaining one or more of particular text in accordance with the scenario, geo-location information associated with the particular text, and number of times of occurrence of the particular text.

3. The computer readable storage device of claim 1, the identifying and converting resources comprising:

converting the resources into RDF format; and linking the converted resources into the multi-relational directed graph.

4. A method of integrating diverse sources of data and data streams comprising:

selecting a scenario for refinement based on a topic, the scenario comprising a text document that describes the topic to be examined, the scenario identifying one or more downstream data users and uses that drive said refinement of the scenario;

creating a multi-relational directed graph based on the scenario;

identifying and converting resources in accordance with the scenario and updating the multi-directed graph based on the converted resources;

identifying data feeds in accordance with the scenario and updating the multi-directed graph based on the data feeds;

creating detectors operable to continuously provide data related to the topic, the detectors receiving said data from said data feeds;

identifying analytical routines that compare information in said data to the scenario and updating the multi-directed graph using the analytical routines, the analytical routines comprising sensors that subscribe to said detectors and responsive to receiving said data, perform at least one of:

comparing, based on alignment, sequences in a data stream to sequences in entities of the multi-relational directed graph, and adding one or more statements to the multi-directed graph based on finding a match;

performing analysis among the entities, literals associated with the scenario and represented as a node in the multi-directed graph and ontologies associated with the scenario and linked to the multi-directed graph, wherein one or more relationship statements are generated between two or more of an entity, a literal, and an ontology in the multi-directed graph; and linking the entities to samples corresponding to events; and identifying data outputs in accordance with the scenario at least based on one of the one or more statements and the one or more relationship statements and defining queries to produce the data outputs from the multi-directed graph, the method further comprising consuming one or more messages from one or more of the sensors indicating a match in said data, the consuming performed by a controller comprising a state machine, and the controller publishing an advisory responsive to finding that all conditions in the scenario are met based on said one or more consumed messages.

5. The method of claim 4, the selecting the scenario comprising:

obtaining one or more of particular text in accordance with the scenario, geo-location information associated with the particular text, and number of times of occurrence of the particular text.

6. The method of claim 4, the identifying and converting resources comprising:

converting the resources into RDF format; and linking the converted resources into the multi-relational directed graph.

7. A system of integrating diverse sources of data and data streams comprising:

a processor; and a module operable to execute on the processor and to select a scenario for refinement based on a topic, the scenario identifying one or more downstream data users and uses that drive said refinement of the scenario, create a multi-relational directed graph based on the scenario, identify and convert resources in accordance with the scenario and update the multi-directed graph based on the converted resources, identify data feeds in accordance with the scenario and update the multi-directed graph based on the data feeds, create detectors operable to continuously provide data related to the topic, the detectors receiving said data from said data feeds, identify analytical routines that compare information in said data to the scenario and update the multi-directed graph using the analytical routines, and identify data outputs in accordance with the scenario and define queries to produce the data outputs from the multi-directed graph, the analytical routines comprising sensors that subscribe to said detectors and responsive to receiving said data, perform at least one of:

comparing, based on alignment, sequences in a data stream to sequences in entities of the multi-relational directed graph, and adding one or more statements to the multi-directed graph based on finding a match;

performing analysis among the entities, literals associated with the scenario and represented as a node in the multi-directed graph and ontologies associated with the scenario and linked to the multi-directed graph, wherein one or more relationship statements are generated between two or more of an entity, a literal, and an ontology in the multi-directed graph; and linking the entities to samples corresponding to events, wherein the data output is identified at least based on one of the one or more statements and the one or more relationship statements, the system further comprising a controller comprising a state machine that consumes one or more messages from one or more of the sensors indicating a match in said data, the controller publishing an advisory responsive to finding that all conditions in the scenario are met based on said one or more consumed messages.

8. The system of claim 7, the module further operable to select the scenario by:

obtaining one or more of particular text in accordance with the scenario, geo-location information associated with the particular text, and number of times of occurrence of the particular text.

9. The system of claim 7, the module further operable to identify and convert resources by:

converting the resources into RDF format; and linking the converted resources into the multi-relational directed graph.

10. The computer readable storage device of claim 1, wherein the data feeds comprise a web crawler, DNA sequencing machine, weather sensor, and satellite imagery.

11. The computer readable storage device of claim 1, wherein the sensors are customized per the scenario.

12. The system of claim 7, wherein said controller is one of a plurality of controllers and said scenario is one of a plurality of instantiated scenarios, wherein one controller runs per an instantiated scenario.

13. The method of claim 4, further comprising connecting the scenario that is refined to another scenario.

14. The method of claim 4, wherein the identifying resources in accordance with the scenario comprises identifying resources required by the scenario but absent in a semantic web.

15. The method of claim 4, wherein the ontologies comprise one or more of a scenario ontology, bio2rdf ontology, or geoname ontology, or combinations thereof.

16. The method of claim 4, wherein the literals comprise one or more of date, match score, or scenario description, or combinations thereof.

* * * * *